United States Patent [19]

Barry et al.

[11] Patent Number: 5,492,763
[45] Date of Patent: Feb. 20, 1996

[54] INFECTION RESISTANT MEDICAL DEVICES AND PROCESS

[75] Inventors: John E. Barry, Waltham; Piran Sioshansi, Lincoln, both of Mass.

[73] Assignee: Spire Corporation, Bedford, Mass.

[21] Appl. No.: 194,788

[22] Filed: Feb. 10, 1994

Related U.S. Application Data

[63] Continuation of Ser. No. 894,822, Jun. 8, 1992, abandoned.

[51] Int. Cl.$^6$ ................................................. B32B 9/00
[52] U.S. Cl. ...................... 428/457; 428/35.7; 428/35.8; 428/35.1; 428/34.7; 604/264; 604/265; 604/280; 604/905
[58] Field of Search ..................... 428/209, 461, 428/465, 435, 457, 458, 459, 460, 434, 35.7, 35.8, 35.1, 34.7; 604/264, 265, 268, 280, 905

[56] References Cited

U.S. PATENT DOCUMENTS

| | | | |
|---|---|---|---|
| 3,557,795 | 1/1971 | Hirsch | 128/335.5 |
| 3,589,975 | 6/1971 | Andrews et al. | 161/165 |
| 3,598,127 | 6/1971 | Wepsci | 604/265 |
| 3,695,921 | 10/1972 | Shepherd et al. | 117/72 |
| 3,699,956 | 10/1972 | Kitrilakis et al. | 604/265 |
| 4,027,393 | 1/1977 | Ellis . | |
| 4,039,699 | 8/1977 | Morimoto et al. | 427/38 |
| 4,054,139 | 10/1977 | Crossley | 604/265 |
| 4,152,478 | 5/1979 | Takagi | 428/221 |
| 4,253,463 | 3/1981 | Kim | 128/348 |
| 4,281,029 | 7/1981 | Takagi et al. | 427/38 |
| 4,374,717 | 2/1983 | Drauglis et al. | 204/192 C |
| 4,411,648 | 10/1983 | Davis et al. | 604/21 |
| 4,440,108 | 4/1984 | Little | 118/719 |

(List continued on next page.)

FOREIGN PATENT DOCUMENTS

| | | |
|---|---|---|
| 0029787 | of 0000 | European Pat. Off. . |
| 206024A | of 0000 | European Pat. Off. . |
| 86107598 | 12/1986 | European Pat. Off. . |
| 0206024 | 12/1986 | European Pat. Off. ............... 604/265 |
| 87307136 | 3/1988 | European Pat. Off. . |
| 3228849A | of 0000 | Germany . |
| 3302567A | of 0000 | Germany . |
| 3228849 | 2/1984 | Germany ............................ 604/265 |
| 3830359 | 12/1989 | Germany ............................ 623/11 |
| PCT/CA91/00453 | 7/1992 | WIPO . |
| PCT/US92/08266 | 4/1993 | WIPO . |
| PCT/US93/00685 | 8/1993 | WIPO . |
| PCT/CA93/00201 | 11/1993 | WIPO . |

OTHER PUBLICATIONS

Maki et al. (Dec. 1973) "Infection Control in Intravenous Therapy", *Ann. Int. Med.*, 79:867–887.
Tully et al. (Mar. 1981) "Complications of Intravenous Therapy with Steel Needles and Telfon® Catheters", *Am. J. Med.*, 70:702–706.
Friedland (1984) "Infusion–Related Phlebitis–Is the In–Line Filter the Solution?", *N.E.J. Med.*, 312:113–115.
Elliott (May 1988) "Intravascular–device infections", *J. Med. Microbiol.*, 27:161–167.

(List continued on next page.)

*Primary Examiner*—Pastrick J. Ryan
*Assistant Examiner*—Patrick Jewik
*Attorney, Agent, or Firm*—Thomas J. Engellenner; John V. Bianco; Lahive & Cockfield

[57] ABSTRACT

A medical device provided with a subsurface bacteriostatic/bactericidal stratum to a predetermined depth is disclosed. The bacteriostatic/bactericidal stratum is introduced into the medical device by ion implantation of sufficient concentration to impart thereto the desired bacteriostatic/bactericidal property. The acquired bacteriostatic/bactericidal property has a useful life coterminal with the device. The treated medical device remains biocompatible, is non-leaching and, depending on the specific device, also is thromboresistant.

9 Claims, 4 Drawing Sheets

U.S. PATENT DOCUMENTS

| | | | |
|---|---|---|---|
| 4,443,488 | 4/1984 | Little et al. | 427/38 |
| 4,603,152 | 7/1986 | Laurin et al. | 604/265 |
| 4,693,760 | 9/1987 | Sioshansi | 148/4 |
| 4,718,905 | 1/1988 | Freeman | 623/6 |
| 4,743,308 | 5/1988 | Sioshansi et al. | 148/4 |
| 4,743,493 | 5/1988 | Sioshansi et al. | 428/217 |
| 4,846,834 | 7/1989 | von Recum et al. | 623/11 |
| 4,855,026 | 8/1989 | Sioshansi | 204/192.11 |
| 4,871,366 | 10/1989 | von Recum et al. | 623/11 |
| 4,872,922 | 10/1989 | Bunker et al. | 148/4 |
| 4,886,505 | 12/1989 | Haynes et al. | 604/265 |
| 4,923,450 | 5/1990 | Maeda et al. | 604/265 |
| 4,936,281 | 6/1990 | Stasz | 128/660.03 |
| 4,994,060 | 2/1991 | Rink et al. | 606/28 |
| 5,049,139 | 9/1991 | Gilchrist | 604/265 |
| 5,049,140 | 9/1991 | Brenner et al. | 604/265 |
| 5,057,106 | 10/1991 | Kasevich et al. | 606/33 |
| 5,067,491 | 11/1991 | Taylor, II et al. | 128/748 |
| 5,069,227 | 12/1991 | Maronian | 165/173 |
| 5,165,952 | 11/1992 | Solomon et al. | 604/265 |
| 5,223,309 | 6/1993 | Farivar | 427/525 |
| 5,236,509 | 8/1993 | Sioshansi et al. | 118/719 |
| 5,308,704 | 5/1994 | Suzuki et al. | 427/525 |

OTHER PUBLICATIONS

Bentivegna (Aug. 1989) "The Vitacuff and Intravascular Catheter–Related Infection", *JAMA Letters*, 262:613–614.

Liedberg et al. (Jan. 1989) "Assessment of Silver–Coated Urinary Catheter Toxicity by Cell Culture" *Urol. Reg.*, 17:359–360.

Solnick–Legg et al. (Apr. 1989) "Ion Beam and Plasma Technology for Improved Biocompatible Surfaces", MRS BULLETIN, pp. 27–30.

Corona et al. (Jul. 1990) "Infections Related to Central Venous Catheters", *Mayo Clin. Proc.*, 65:979–986.

Johnson et al. (Nov. 1990) "Prevention of Catheter–Associated Urinary Tract Infection with a Silver Oxide–Coated Urinary Catheter: Clinical and Microbiologic Correlates", *J. Infect. Dis.*, 162:1145–1150.

Liedberg et al. (1990) "Silver Alloy Coated Catheters Reduce Catheter–Associated Bacteriuria", *Brit. J. Urol.* 65:379–381.

Putterman (1990) "Central venous catheter related sepsis: A clinical review", *Resuscitation*, 20:1–16.

Haywood "Dual IBAD Makes Good Coatings", *Advanced Materials and Processes*, vol. 138, Issue 6, publication of The Materials Information Society, (Feb. 6, 1991).

Mahan et al. (Mar. 1991) "Factors in Pin Tract Infections", *Orthopedics*, 14:305–308.

Murphy et al. (Mar. 1991) "The Small Pin Circular Fixator For Proximal Tibial Fractures With Soft Tissue Compromise", *Orthopedics*, 14:273–280.

IBAD Brochure, Spire Corporation, Bedford, MA, published Mar. 8, 1991.

SPI–ARGENT™ Brochure, published Oct. 9, 1992.

SPI–ARGENT™ Technical Brochure, published Apr. 23, 1993.

Yoshiaki Suzuki, Masahiro Kosakabe, Masaya Iwaki, Kiyoko Kosakabe, Hiromichi Akiba, and Masaaki Suzuki, "Effects of Ion Implantation on Protein Adsorption onto Silicone Rubber", Mast. Res. Soc. Symp. Proc., vol. 110, MRS, 1989.

INFECTION RESISTANT MEDICAL DEVICES AND PROCESS

This application is a file wrapper continuation of U.S. patent application Ser. No. 07/894,822, filed on Jun. 8, 1992, now abandoned.

BACKGROUND OF THE INVENTION

1. Field of the Invention

The present invention relates generally to medical devices designed to come into contact with body tissue and, more particularly, to medical devices which have been rendered bacteriostatic/bactericidal and a process for making them so.

2. The Prior Art

As known, infections, such as nosocomial infections (infections originating in a hospital), result from polymeric, metallic and/or ceramic implanted devices, including external fixation devices, indwelling urological catheters and the like, being placed in the body. Most medical device manufacturers have shied away from employing bacteriostatic compounds as antimicrobial agents in such indwelling devices because of the difficulties associated with producing an adherent, long lasting film on such polymeric, metallic and/or ceramic surfaces.

Heretofore, efforts directed at fighting infection associated with the use of implanted devices tended to reduce their biocompatibility. The balancing of these two goals has been one of the challenges facing the medical practitioner.

In related co-pending applications, all assigned to a common assignee, Spire Corporation, Bedford, Massachusetts, and having at least one common co-inventor, there are disclosed and claimed efforts directed at the dry-coating metallization of polymeric implants to improve their biocompatibility and to reduce phlebitis and infection, and to provide bacteriostatic/bactericidal coatings on implants, both by ion-beam-assisted deposition (IBAD), see Ser. No. 07/663,361, filed Mar. 1, 1991, Mohammed Farivar and Piran Sioshansi, entitled "Metallized Polymeric Implants, Methods and Apparatus," and Ser. No. 07/780,275, filed Oct. 18, 1991, Piran Sioshansi et al, entitled "Bactericidal Coatings for Implants." The disclosures of both of said applications Ser. Nos. 07/663,361 and 07/780,275 are incorporated herein by reference.

Another co-pending application, Ser. No. 07/728,098, filed Jul. 10, 1991, also assigned to said common assignee, Spire Corporation, Bedford, Mass. and having one common co-inventor, discloses an ion implantation process designed to alter silicone rubber's surface to that being characterized by low friction, being hydrocompatible, inkable, deformable, antithrombotic and more wear resistant.

The use of ion beam processing is well known and is widespread. The common assignee herein, Spire Corporation of Bedford, Massachusetts, is one of the pioneers in the field of ion beam technology. A plasma-supported ion beam technique for coating industrial cutting tools with a thin layer of cubic boron nitride to improve the tools' cutting properties is disclosed in U.S. Pat. No. 4,440,108, of Roger G. Little et al, granted Apr. 3, 1984, and assigned to said Spire Corporation. A plasma-ion deposition process of large-grain, thin semiconductor films directly on low-cost amorphous substrates is disclosed in U.S. Pat. No. 4,443,488, also of Roger G. Little et al, granted Apr. 17, 1984 and assigned to said Spire Corporation. A process of preventing surface discoloration in titanium orthopaedic implants by ion implantation is disclosed in U.S. Pat. No. 4,693,760 of Piran Sioshansi, granted Sep. 15, 1987 and assigned to said Spire Corporation. An ion implantation process for plastics to enhance their surface hardness and their resistance to chemical attack is disclosed in U.S. Pat. No. 4,743,493 of Piran Sioshansi et al, granted May 10, 1988 and assigned to said Spire Corporation. A process for passivating the electrochemically active surface of metal alloys so as to inhibit their corrosion is disclosed in U.S. Pat. No. 4,743,308 of Piran Sioshansi et al, granted May 10, 1988 and assigned to said Spire Corporation. A sputter-enhanced ion implantation process, primarily of ball bearings, without the use of a separate evaporation system is disclosed in U.S. Pat. No. 4,855,026 of Piran Sioshansi, granted Aug. 8, 1989 and assigned to said Spire Corporation. An improved method and apparatus for the uniform ion implantation of spherical surfaces, such as ball bearings, is disclosed in U.S. Pat. No. 4,872,922 of Stephen N. Bunker et al, granted Oct. 10, 1989 and assigned to said Spire Corporation. A method of depositing an ionized cluster on a substrate is disclosed in U.S. Pat. No. 4,152,478 of Toshinori Takagi, granted May 1, 1979. And a method of coating a substrate with a stoichiometric compound is disclosed in U.S. Pat. No. 4,281,029 of Toshinori Takagi et al, granted Jul. 28, 1981.

SUMMARY OF THE INVENTION

It is a principal object of the present invention to overcome the above disadvantages by providing polymeric, metallic and/or ceramic medical devices designed to come into contact with body tissue with a permanent subsurface bacteriostatic/bactericidal stratum in a manner that the devices nonetheless remain biocompatible.

More specifically, it is an object of the present invention to provide a medical device formed from either polymeric, metallic and/or ceramic materials, or a combination of such materials, with a permanent subsurface bacteriostatic/bactericidal stratum to a predetermined depth and introduced therein by injecting bacteriostatic/bactericidal ions of sufficient concentration into the surface of the medical device without adversely affecting the biocompatibility of the device. Albeit the level of concentration of the injected bacteriostatic/bactericidal ions to impart the desired bacteriostatic/bactericidal property to the medical device depends on the material thereof, a minimum sufficient level of bacteriostatic/bactericidal ion concentration is about $1 \times 10^{15}$ ions/cm$^3$. Since it does not leach, the acquired bacteriostatic/bactericidal property of the medical device remains effective for the useful life of the device. Preferably, the bacteriostatic/bactericidal ions comprise at least one member of the class of Ag, Au, Cu, Pt, Ir, Mg, Pd and its respective compounds and alloys. Preferably, the injection of the bacteriostatic/bactericidal ions is effected in a chamber evacuated to a vacuum of at least about $10^{-4}$ torr. Depending on the substrate, the treated medical device also is thromboresistant and wear resistant.

Other objects of the present invention will in part be obvious and will in part appear hereinafter.

The invention accordingly comprises the polymeric, metallic and/or ceramic medical devices provided with subsurface bacteriostatic/bactericidal strata of the present disclosure, its components, parts and their interrelationships, the scope of which will be indicated in the appended claims.

BRIEF DESCRIPTION OF THE DRAWINGS

For a fuller understanding of the nature and objects of the present invention, reference is to be made to the following detailed description, which is to be taken in connection with the accompanying drawings, wherein.

DETAILED DESCRIPTION OF THE PREFERRED EMBODIMENTS

In general, the present invention relates to medical devices designed to come into contact with body tissue which devices have been provided with bacteriostatic/bactericidal properties without however featuring any bacteriostatic/bactericidal coatings thereon.

More specifically, the present invention relates to medical devices formed of metallic, ceramic, and/or polymeric materials, or a combination of such materials, which have been provided with a subsurface bacteriostatic/bactericidal stratum to a predetermined depth. The subsurface bacteriostatic/bactericidal stratum preferably is introduced into the surface of the medical device by the injection of bacteriostatic/bactericidal ions of sufficient concentration to impart the desired level of bacteriostatic/bactericidal property to the device. The treated medical device with its acquired bacteriostatic/bactericidal property, is non-leaching, biocompatible and, depending on the substrate, is thromboresistant.

In the use of medical devices designed to enter the human body, investigations have shown that the most significant complications involved pin tract infections and catheter introduced infection. The predominant organism found in pin tract infection was *Staphylococcus epidermidis* considered non-virulant, followed by virulant *Staphylococcus aureus* and *Escherichia coli*. Catheters also may be colonized by means of seeding through the blood from distant sites of infection. Such distant seeding appears to be more common for yeast than it is for *S. aureus*. Enteric bacteria, such as enterococci, *Escherichia coli* and Klebsiella also may infect catheters by hematogenous seeding.

Phlebitis and cellulitis represent but the onset of infusion-associated infections. They are likely to be followed by fever, sepsis, infiltration, bacteremia, septic thrombophlebitis, disseminated infection and septicemia. Vascular prostheses and artificial surfaces used in cardio-pulmonary bypass and renal dialysis systems also are frequently associated with thromboembolic complications. An example of pin tract infection caused by the virulent bacillus *Escherichia coli* is illustrated in FIGS. 7 and 8.

Figure 7:
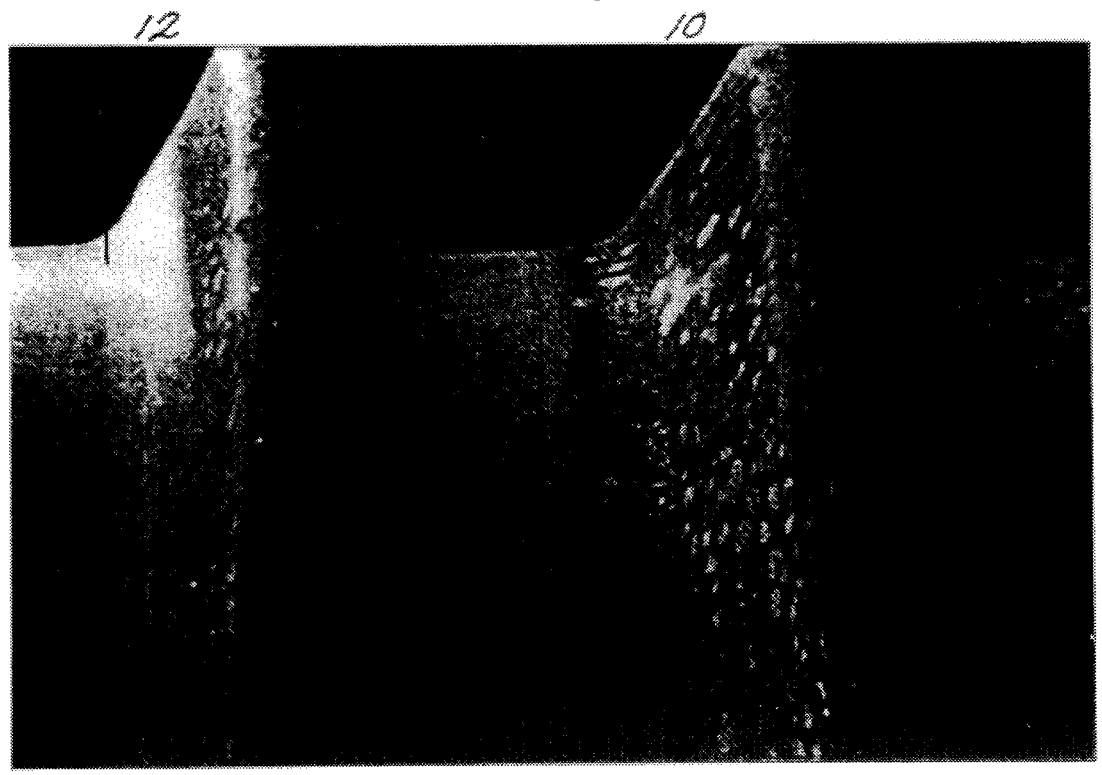
FIG. 7 is a picture, on an enlarged scale, of an external fixation pin, not possessing bacteriostatic/bactericidal properties and showing the signs of infection.
Figure 8:
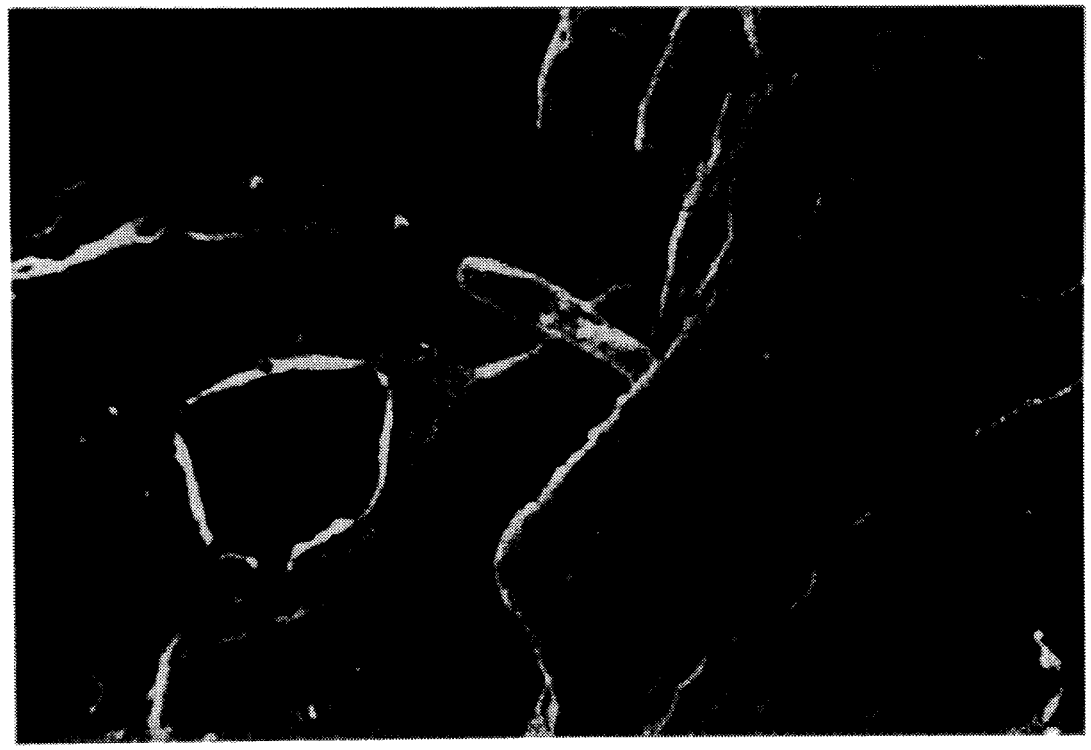
FIG. 8 illustrates a portion of the infected surface, on an enlarged scale, of the external fixation pin of FIG. 7.

FIG. 7 illustrates, on an enlarged scale, visible signs of infection, as at 10, on the surface of a conventional external fixation pin 12 after removal from a patient. A portion of the infected area 10 of the pin 12, on a still further enlarged scale and illustrating the offending bacillus, is shown in FIG. 8.

Figure 1:
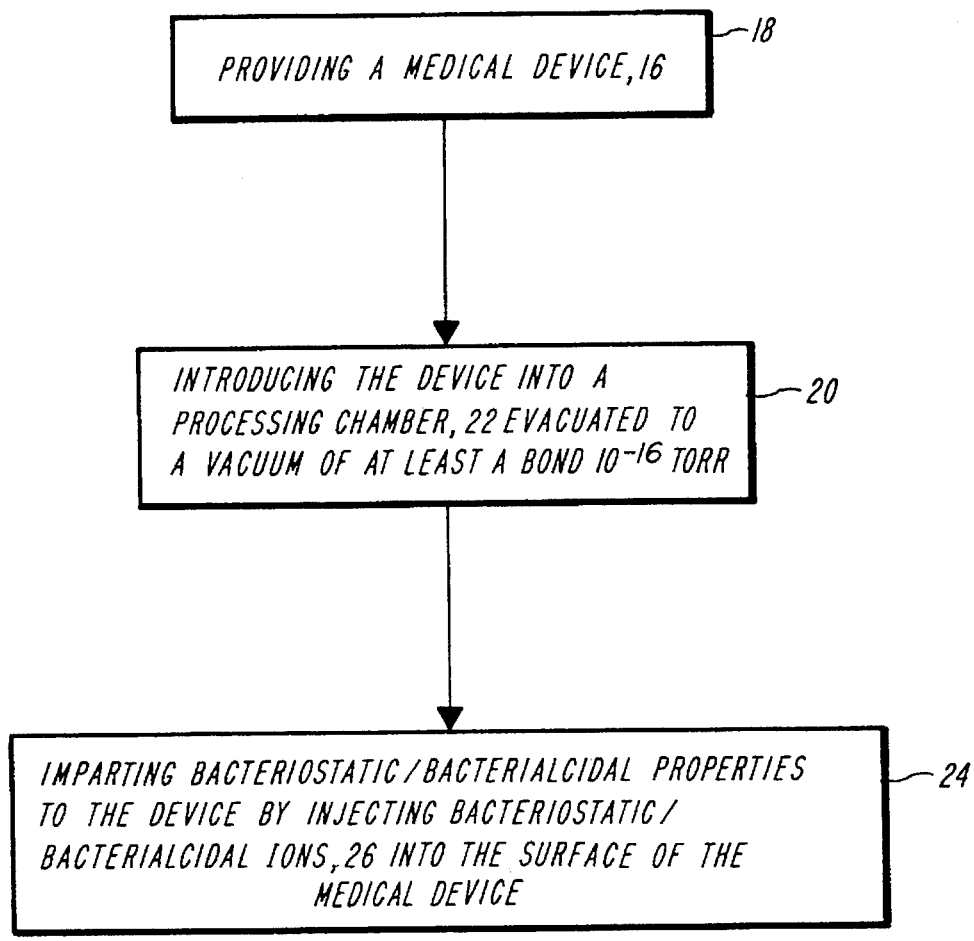
FIG. 1 is a flow diagram of a preferred process of imparting bacteriostatic/bactericidal properties to a medical device.

Infection resistant medical devices according to the invention are produced according to a preferred process as graphically illustrated in a flow diagram in FIG. 1.

Figure 4:
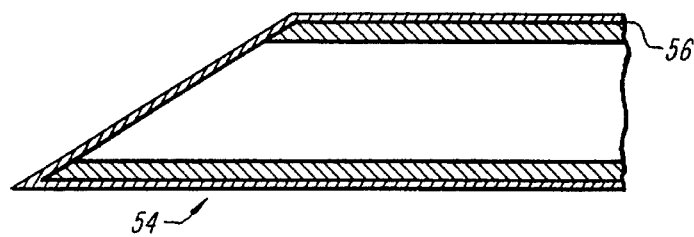
FIG. 4 is a longitudinal cross section, on an enlarged scale, of a typical cannula tip injected by bacteriostatic/bactericidal ions according to the invention.
Figure 5:
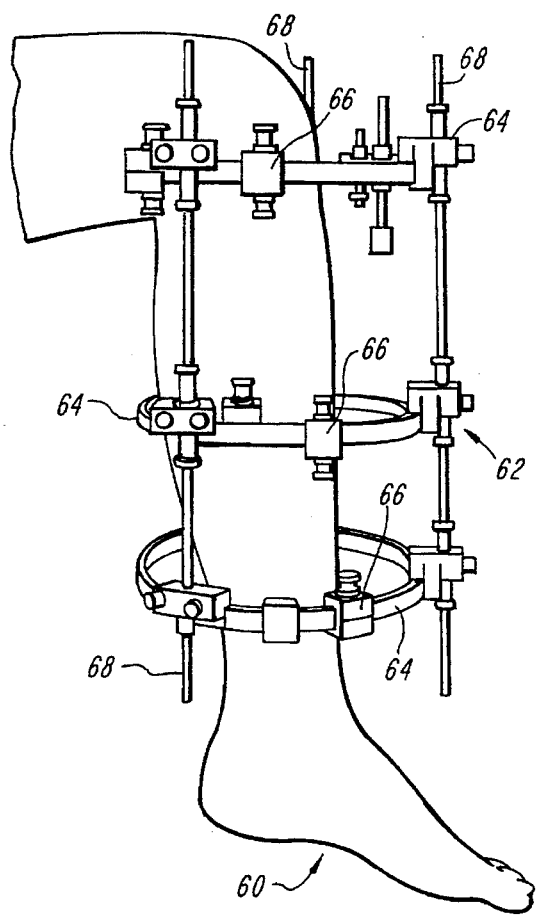
FIG. 5 illustrates a leg below the knee to which an external fixation device has been secured.
Figure 6:
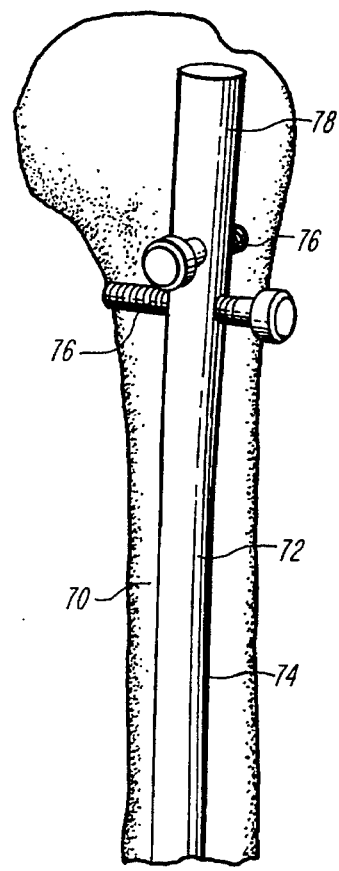
FIG. 6 illustrates a fragmentary vertical section of a humerus with an intramedullary fixation nail implanted therein.

The inventive process applies to any medical device 16 intended to come into contact with and/or enter into body tissue. Thus, all biomedical devices and components, formed of polymer, metal, or ceramic, designed to penetrate or enter into the body, are included herein. The biomedical components illustrated in FIGS. 4–6 are merely representative of this class, which also includes metallic needles, urological catheters, metallic percutaneous connectors, polymeric drug dispensers, optical lens cases, and ceramic and metallic counterfaces in joint replacements, such as for the hip or the knee.

The inventive process for imparting bacteriostatic/bactericidal properties to medical devices designed to come into contact with body tissue (be it skin, muscle, bone or blood) essentially comprises providing 18 such a medical device 16, introducing 20 the device 16 into a processing chamber 22 evacuated to a vacuum of at least about 10 torr, and imparting 24 bacteriostatic/bactericidal properties to the device 16 by injecting bacteriostatic/bactericidal ions 26 into the surface of the medical device 16.

Figure 2:
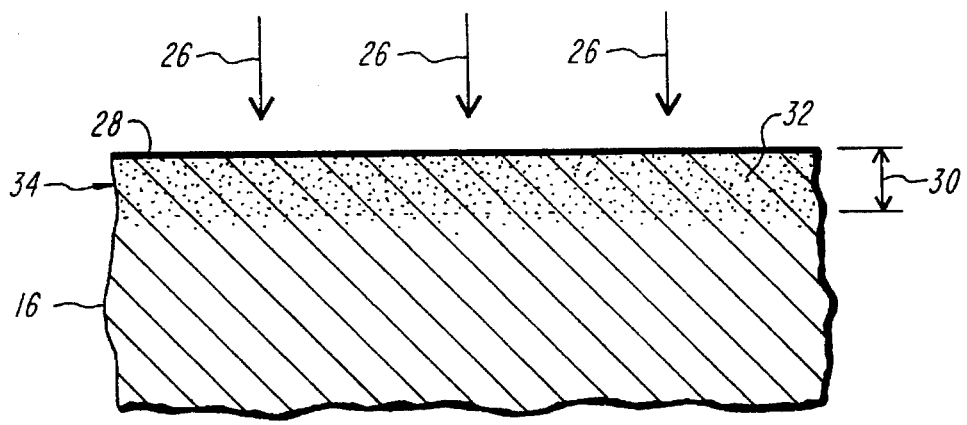
FIG. 2 is a fragmentary section, on an enlarged scale, of a surface of a medical device being injected by bacteriostatic/bactericidal ions.

In FIG. 2 is illustrated, in fragmentary section and on an enlarged scale, a surface 28 of the medical device 16 being injected by a plurality of bacteriostatic/bactericidal ions 26 to a preferred depth, as indicated by an arrow 30, of at least about 0.01 micron below the surface 28. The injected bacteriostatic/bactericidal ions are illustrated by a plurality of dots 32. It is the concentration (defined in ions/cm$^3$) of these injected bacteriostatic/bactericidal ions 32 below the surface 28 that creates a subsurface bacteriostatic/bactericidal stratum 34 in the medical device 16, which bacteriostatic/bactericidal stratum 34 imparts to the device 16 the desired bacteriostatic/bactericidal properties. The sufficiency of this concentration of the injected bacteriostatic/bactericidal ions 32 to impart the desired bacteriostatic/bactericidal properties to the medical device 16 depends, in the first instance, whether the device 16 is formed of metal, polymer or ceramic, and further in the specifics of the metal, the polymer or the ceramic, and still further on the specific bacteriostatic/bactericidal ion being employed. The following represents the class of bacteriostatic/bactericidal ions 26 employed in the process consisting of silver, gold, copper, platinum, iridium, magnesium and palladium, and their respective compounds and alloys.

Most medical devices and a great many biomedical components are formed of surgical stainless steel, titanium, cobalt-chromium, aluminum or zirconium. Others, such as catheters, are formed of polyurethane, polyethylene, silicone rubber, PTFE and PVC, latex, nylon, or a combination of these materials and some metal and/or ceramic.

Figure 3:
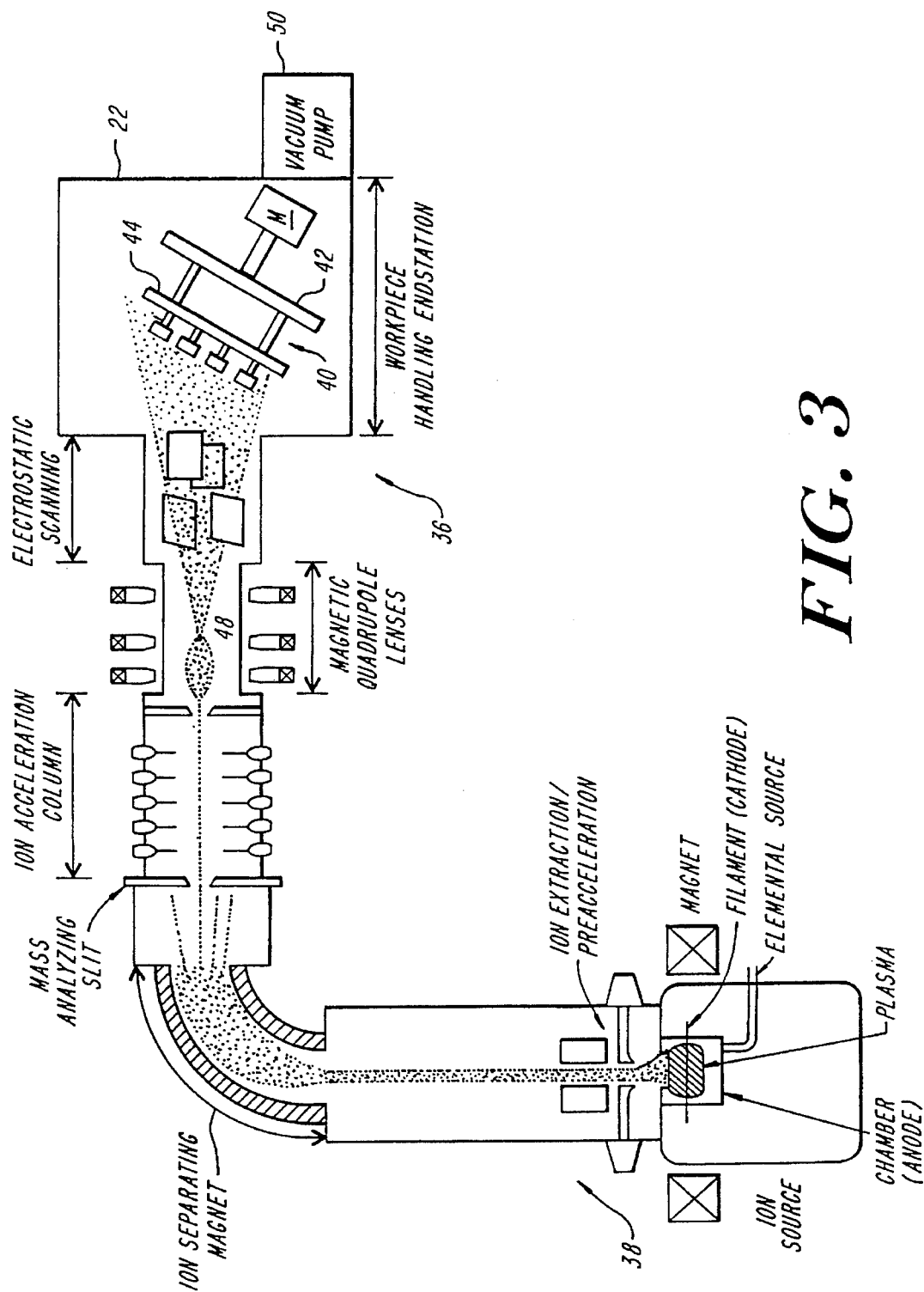
FIG. 3 is a schematic diagram of a preferred apparatus useful for injecting bacteriostatic/bactericidal ions into medical devices.

The process of the invention designed to impart the desired bacteriostatic/bactericidal properties to medical devices is preferably carried out in the processing chamber 22 of a specially designed endstation 36 of a suitable high current ion implanter 38, such as a Varian-Extrion 200 kV implanter, an Eaton-Nova implanter or like an instrument illustrated in FIG. 3. This ion implanter 38 can be the same as, or an adaption of the one illustrated in and described in U.S. Pat. No. 4,693,760, granted Sep. 15, 1987 and assigned to the common assignee, Spire Corporation of Bedford, Mass.

Within the processing chamber 22, a suitable fixture 40 is mounted on a base 42 designed for rotation by a suitable motor (M) and for cooling a base plate 44. On the base plate 44 preferably are mounted a plurality of appropriately shaped workpiece holders 46, each preferably consisting of plates designed to hold a multiplicity of parts. These workpiece holders 46 are designed to hold securely a plurality of medical devices 16 and directly to expose these devices 16 to an incoming ion beam 48 of bacteriostatic/bactericidal ions. The shape of the particular workpiece holders 46 secured to the base plate 44 will of course depend upon the shape of the particular medical device 16 worked on at that time.

With the medical devices 16 properly secured within the chamber 22, a required vacuum environment within the processing chamber 22 is created by means of a vacuum pump 50, operatively connected to the chamber 22. With the aid of the pump 50, the processing chamber 22 is preferably evacuated to a vacuum pressure of at least $10^{-6}$ torr. Preferably, the vacuum pump 50 is an oil-free type designed to avoid the possibility of introducing surface contamination onto the device 16 to be an ion implanted.

The surfaces 28 of the medical devices 16 are then exposed to the ion beam 48 of bacteriostatic/bactericidal ions so as to create the subsurface bacteriostatic/bactericidal stratum 34 therein. Preferably, the ion beam 48 possesses an energy from about 5 keV to about 200 keV, delivering a dose from about $3 \times 10^{14}$ to about $5 \times 10^{17}$ ions per square centimeter. The above mentioned ion beam energy and ion dose are intended to achieve a current density on the respective surfaces of the devices 16 from about 0.01 microampere per square centimeter to about 0.5 microampere per square centimeter. The preferred concentration of the injected bacteriostatic/bactericidal ions 32 within the subsurface bacteriostatic/bactericidal stratum 34 is at least about $1 \times 10^{15}$ ions per cubic centimeters. The preferred depth 30 of the subsurface bacteriostatic/bactericidal stratum 34 is at least about 0.01 micron to about two microns, depending on the material adjacent the surface 28 of the medical device 16. The ion implantation process of the invention is effected over a time period from about one minute to about 20 hours, depending on the material adjacent the surface 28 of the device 16 and on a selected combination of ion dose, ion beam current energy, and the particular bacteriostatic/bactericidal ion 26 being employed.

Illustrative Samples of Medical Devices of FIGS. 4–6

In FIG. 4, there is illustrated, in longitudinal cross section and on an enlarged scale a medical device in the form of a cannula tip 54. "Cannula" as used herein is a general term employed in the medical devices field that defines all types of catheters, percutaneous devices, draining tubes and steel needles. The cannula tip 54 has been provided according to the invention, with a subsurface bacteriostatic/bactericidal stratum 56.

In FIG. 5 is illustrated a limb 60 fractured in an accident. The skeletal fracture of the limb 60 is shown being stabilized by an external fixation device 62. The external fixation device 62 essentially comprises a plurality of ¾ rings 64, each securing at least two transfixion pins 66 passing through the limb 60 and thereby stabilizing the affected internal skeletal fracture segments. It is primarily these pins 66 that cause the pin tract infections. The rings 64 are secured to one another by three threaded connecting rods 68. Preferably, each of these connected component parts of the external fixation device 62 also has been provided, according to the invention, with a subsurface bacteriostatic/bactericidal stratum.

And in FIG. 6, a humerus 70 is illustrated in fragmentary vertical section, with an intramedullary fixation nail 72 implanted in its intramedullary canal 74 and secured therein by suitable screws 76. The intramedullary fixation nail 72 and its associated screws 76, preferably all formed of surgical stainless steel, have been provided with a subsurface bacteriostatic/bactericidal stratum 78 according to the invention.

With the provision of bacteriostatic/bactericidal properties according to the invention, each of the above-illustrated representative medical devices, when implanted, avoids the onset of infections illustrated in FIGS. 7 and 8.

EXAMPLE I

A medical device, such as a cannula formed of a polymer has been provided with a subsurface bacteriostatic/bactericidal stratum, as follows:

Cannula (a catheter) formed of silicone rubber material; Subsurface bacteriostatic/bactericidal stratum:

| | | |
|---|---|---|
| a/ | depth: | 0.2 micron |
| b/ | injected bacteriostatic/bactericidal ions: | Hg |
| c/ | concentration of the injected bacteriostatic/bactericidal ions: | $5 \times 10^{16}$ ions/cm$^3$ |
| d/ | vacuum in implantation chamber: | $10^{-6}$ torr |
| e/ | dose of ions: | $1 \times 10^{16}$ ions/cm$^2$ |
| f/ | particle energy of the injected ions: | 50 keV |
| g/ | current density: | 0.1 UA/cm$^2$ |

Process produces a low friction, non-tacky surface. The subsurface bacteriostatic/bactericidal stratum of the medical device remains biocompatible and non-leaching, is also thromboresistant.

EXAMPLE II

A medical device, such as a cannula formed of metal has been provided with a subsurface bacteriostatic/bactericidal stratum, as follows:

Cannula (a catheter) formed of stainless steel material; Subsurface bacteriostatic/bactericidal stratum:

| | | |
|---|---|---|
| a/ | depth: | 0.2 micron |
| b/ | injected bacteriostatic/bactericidal ions: | Au |
| c/ | concentration of the injected bacteriostatic/bactericidal ions: | $3 \times 10^{16}$ ions/cm$^3$ |
| d/ | vacuum in implantation chamber: | $10^{-6}$ torr |
| e/ | dose of ions: | $1 \times 10^{17}$ ions/cm$^2$ |
| f/ | particle energy of the injected ions: | 50 keV |
| g/ | current density: | 0.1 uA/cm$^2$ |

The subsurface bacteriostatic/bactericidal stratum of the medical device remains biocompatible and non-leaching, is also wear resistant.

EXAMPLE III

A medical device, such as a surgical pin formed of metal has been provided with a subsurface bacteriostatic/bactericidal stratum, as follows:

| | Surgical pin formed of stainless steel material; Subsurface bacteriostatic/bactericidal stratum: | |
|---|---|---|
| a/ | depth: | 0.1 micron |
| b/ | injected bacteriostatic/ bactericidal ions: | Ag |
| c/ | concentration of the injected bacteriostatic/bactericidal ions: | $6 \times 10^{16}$ ions/cm$^3$ |
| d/ | vacuum in implantation chamber: | $10^{-6}$ torr |
| e/ | dose of ions: | $2 \times 10^{17}$ ions/cm$^2$ |
| f/ | particle energy of the injected ions: | 100 keV |
| g/ | current density: | 0.2 uA/cm$^2$ |

The subsurface bacteriostatic/bactericidal stratum of the medical device remains biocompatible and non-leaching, is also wear and fatigue resistant.

EXAMPLE IV

A medical device, such as a dental implant formed of ceramic has been provided with a subsurface bacteriostatic/bactericidal stratum, as follows:

| | Dental implant formed of ceramic (such as AlO$_2$) material; Subsurface bacteriostatic/bactericidal stratum: | |
|---|---|---|
| a/ | depth: | 0.1 micron |
| b/ | injected bacteriostatic/ bactericidal ions: | Mg |
| c/ | concentration of the injected bacteriostatic/ bactericidal ions: | $3 \times 10^{15}$ ions/cm$^3$ |
| d/ | vacuum in implantation chamber: | $10^{-6}$ torr |
| e/ | dose of ions: | $1 \times 10^{16}$ ions/cm$^2$ |
| f/ | particle energy of the injected ions: | 100 keV |
| g/ | current density: | 0.1 uA/cm$^2$ |

The subsurface bacteriostatic/bactericidal stratum of the medical device remains biocompatible and non-leaching.

EXAMPLE v

A medical device, such as an ear ventilation tube formed of teflon or silicone rubber, has been provided with a subsurface bacteriostatic/bactericidal stratum, as follows:

| | An ear ventilation tube formed of teflon or silicone rubber material; Subsurface bacteriostatic/bactericidal stratum: | |
|---|---|---|
| a/ | depth: | 0.2 micron |
| b/ | injected bacteriostatic/ bactericidal ions: | Ar+ |
| c/ | concentration of the injected bacteriostatic/bactericidal ions: | $5 \times 10^{16}$ ions/cm$^3$ |
| d/ | vacuum in implantation chamber: | $5 \times 10^{-6}$ torr |
| e/ | dose of ions: | $1 \times 10^{17}$ ions/cm$^2$ |
| f/ | particle energy of the injected ions: | 50 keV |
| g/ | current density: | 0.1 uA/ CM$^2$ |

The subsurface bacteriostatic/bactericidal stratum of the medical device remains biocompatible and non-leaching.

Thus it has been shown and described a medical device which has been provided with a subsurface bacteriostatic/bactericidal stratum to a predetermined depth and a method to effect the same, which product and process satisfy the objects and advantages set forth above.

Since certain changes may be made in the present disclosure without departing from the scope of the present invention, it is intended that all matter described in the accompanying drawings, be interpreted in an illustrative and not in a limiting sense.

What is claimed is:

1. A biomedical implant for insertion within a subject, comprising an implantable biocompatible structure formed from a unitary polymeric material having a tissue-engaging outer surface, the tissue-engaging outer surface having embedded therein atoms of a bactericidal material to form a substantially nonleaching bactericidal subsurface stratum, the atoms extending only partially through the implantable biocompatible structure to a predetermined depth from the tissue engaging outer surface.

2. The biomedical implant of claim 1 wherein the atoms of the bactericidal material extend below the tissue-engaging outer surface to a depth less than about 2.0 microns.

3. The biomedical implant of claim 1 wherein the atoms of the bactericidal material are embedded within the tissue-engaging outer surface by implantation of ions with a current density of at least about 0.01 µA/cm$^2$.

4. The biomedical implant of claim 1 wherein the atoms of the bactericidal material comprise metal atoms.

5. The biomedical implant of claim 1 wherein the atoms of the bactericidal material comprise at least one of silver, gold, copper, platinum, iridium, magnesium, and palladium atoms.

6. A biomedical implant for insertion within a subject, comprising an implantable member formed from a unitary polymeric material having a tissue-engaging outer surface having embedded therein atoms of a bactericidal material, the atoms being embedded by ion implantation, and being secured within the member and extending into the tissue-engaging outer surface to a depth between about 0.01 microns and about 2.0 microns, whereby the atoms of the bactericidal material remain effective for the useful life of the implantable member.

7. The biomedical implant of claim 6 wherein the atoms of the bactericidal material have a concentration of at least $10^{15}$ ions/cm$^3$.

8. The biomedical implant of claim 6 wherein the atoms of the bactericidal material comprise metal atoms.

9. The biomedical implant of claim 6 wherein the atoms of the bactericidal material comprise at least one of silver, gold, copper, platinum, iridium, magnesium and palladium atoms.

* * * * *